United States Patent [19]

Roberto et al.

[11] Patent Number: 5,011,838
[45] Date of Patent: Apr. 30, 1991

[54] PHARMACOLOGICALLY ACTIVE 2-SUBSTITUTED 3-(2-ETHOXYETHYL) IMIDAZO(4,5-B)PYRIDINES AND PHARMACEUTICAL COMPOSITIONS CONTAINING THEM

[75] Inventors: Giani Roberto; Parini Ettore; Borsa Massimiliano; Lavezzo Antonio, all of Milan, Italy

[73] Assignee: Dompé Farmaceutici S.p.A., Milan, Italy

[21] Appl. No.: 519,995

[22] Filed: May 7, 1990

[30] Foreign Application Priority Data

May 8, 1989 [DE] Fed. Rep. of Germany ....... 3915025

[51] Int. Cl.$^5$ .................. A61K 31/44; A61K 31/535; C07D 471/04
[52] U.S. Cl. ................... 514/234.2; 514/303; 544/127; 546/118
[58] Field of Search ......... 546/118; 544/127; 514/303, 234.2

[56] References Cited

U.S. PATENT DOCUMENTS 4,555,660 12/1985 Janssens et al. .............. 514/253
4,695,575 9/1987 Janssens et al. .............. 514/322

FOREIGN PATENT DOCUMENTS 0282133 9/1988 European Pat. Off. .
0307014 3/1989 European Pat. Off. .

*Primary Examiner*—Mary C. Lee
*Assistant Examiner*—Lenora Miltenberger
*Attorney, Agent, or Firm*—Armstrong, Nikaido, Marmelstein, Kubovcik & Murray

[57] ABSTRACT

2-substituted 3-(2-ethoxyethyl)imidazo[4,5-b] pyridine derivatives of the formula

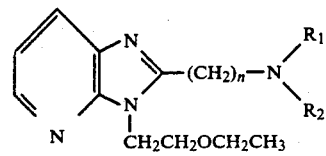

(I)

wherein
n is an integer of from 1 to 5 inclusive
$R_1$ and $R_2$ represent each a saturated or unsaturated alkyl radical containing from 1 to 4 carbon atoms or they form, together with the adjacent nitrogen atom an optionally substituted heterocyclic ring and
the corresponding non-toxic pharmaceutically acceptable acid addition salts.

The compounds of formula (I) are endowed with antiallergic and antihistaminic activity.

7 Claims, No Drawings

PHARMACOLOGICALLY ACTIVE 2-SUBSTITUTED 3-(2-ETHOXYETHYL) IMIDAZO(4,5-B)PYRIDINES AND PHARMACEUTICAL COMPOSITIONS CONTAINING THEM

The present invention relates to novel 2-substituted 3-(2-ethoxyethyl)imidazo [4,5-b] piridine derivatives which belong to the class of formula

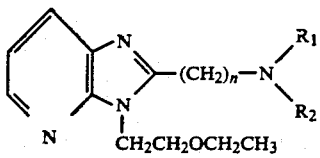

wherein
n is an integer of from 1 to 5 inclusive
$R_1$ and $R_2$ represents each a saturated or unsaturated alkyl radical containing from 1 to 4 carbon atoms or they, together with the adjacent nitrogen atom may form an optionally substituted heterocyclic ring, and
to the corresponding non-toxic pharmaceutically acceptable acid addition salts.

More particularly the heterocyclic ring is represented by the pyrrolidine, morpholine and piperidine ring which may be substituted by lower alkyl radicals. With the term lower alkyl radical it is meant an alkyl radical containing 1 to 3 carbon atoms.

The saturated alkyl radical is preferably represented by methyl, ethyl and propyl, while the unsaturated alkyl radical is preferably allyl radical.

Among the non-toxic, pharmaceutically acceptable acid addition salts of the compounds (I) are preferred fumarate, maleate, succinate and hydrochloride: among them the fumarate is particularly preferred.

The compounds of formula (I) are easily prepared starting from 2,3-diaminopyridine which is reacted in warm conditions with a suitable acid HOOC-$(CH_2)_n$—$N(R_1)R_2$ wherein n, $R_1$ and $R_2$ have the above described meanings and then treating the so formed imidazopyridine (II) in alkaline ambient, in a suitable organic solvent, with a suitable halide $HalCH_2CH_2OCH_2CH_3$ where Hal is a halogen atom, preferably a chlorine atom.

The process may be schematically described as follows:

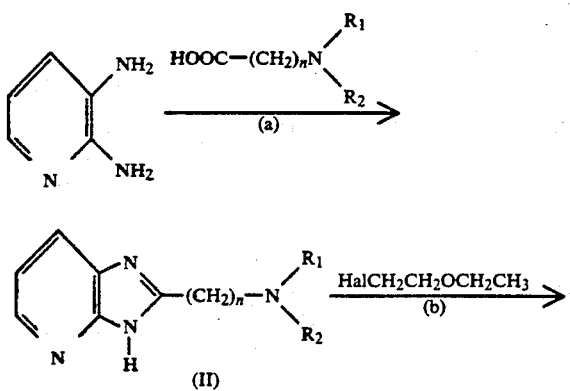

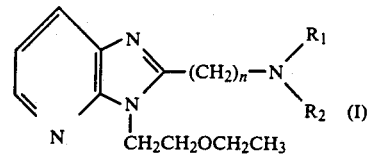

Reaction (a) is carried out at high temperature, generally between 150° and 200° C., while reaction (b) is performed at a lower temperature, generally between 80° and 100° C., in a suitable aprotic solvent, preferably N,N-dimethylformamide and in the presence of sodium hydride.

The compounds (I) have shown to possess an interesting antiallergic and antihistaminic activity. These activities have been evaluated studying either the effect on the mortality induced by histamine and the effect on the mortality induced by compound 48/80. The effect on the sleeping time and the acute toxicity ($LD_{50}$) have been also determined.

The methods followed in carrying out the above tests are here below described.

Effect on the Mortality Induced by Histamine

The method described by Romer D. et al. (Med. Welt. 17,791, 1966) was followed and the tests were carried out on male albino guinea pigs (Dunkin-Hartley), weighing 350 to 450 g which were kept in cages with a grid floor, on an empty stomach for 24 hours with water ad libitum. The compounds under examination have been orally administered to the animals, dissolved in 0.5% carboxymethylcellulose, 60 minutes before intravenous administration of 1.25 mg/kg of histamine dihydrochloride in saline solution. In the control animals, treated with carboxymethylcellulose, the intravenous administration of histamine dihydrochloride induced a 100% mortality.

It has been evaluated $ED_{50}$, which corresponds to the amount of the compound able to inhibit to 50% the mortality induced by histamine: estimation of $ED_{50}$ has been made applying the 'probit' method (Finney D. J. "Statistical method in biological assay", pg 512,1957).

Mortality Inhibition by Compound 48/80

For evaluating the protection to the mortality induced by compound 48/80 administration the method described by C. J. E. Niemegeers et al. (Arch. Int. Pharmacodyn, 234,164,1978) was followed.

Sprague Dawley Nos male rats (Nossan, Correzzana, Milano) weighing 140 to 150 g, divided into groups of 10 animals each, on an empty stomach for 24 hours with water "ad libitum", were kept in cages with a grid floor, and treated intravenously with 2 mg/kg of compound 48/80 (1 ml/rat).

The animals were kept under observation for 4 hours taking note of their mortality. The results were expressed as the number of animals dead with respect to the number of treated animals. Compounds under examination or the carrier were administered half an hour before administration of compound 48/80 by intraperitoneal route, dissolved in $H_2O$ (5 ml/kg). The experimental data were submitted to the variance analysis and to subsequent multiple comparisons according to Dunnet (D. J. Finney, in "Statistical Methods in Biological assay", Ed. L. Griffin and Co. Ltd., pag. 152,1957, Edition Ames Iowa, 1971).

Effect on the Sleeping Time Induced by Pentobarbital

The tests were carried out on male mice Swiss-Nos (Nossan, Correzzana, Milano) weighing 20-24 g, on an empty stomach for 18 hrs, according to the method described by R. Turner ("Screening Methods in Pharmacology", Acad. Press, pg 70,1965). The sleeping was induced by intraperitoneal administration of 40 mg/kg sodium pentobarbital. The narcosis start was considered from the moment when the animal, lying on its back, lost its straightening reflex. The narcosis end was considered from the moment when the animal recovered such reflex.

The carrier or the compounds under examination were intraperitoneally administered (25 mg/kg) 30 minutes before the pentobarbital administration.

The resulting data are expressed as sleeping time increase percent of the treated animals in comparison with the controls.

Evaluation of the Lethal Dose$_{50}$ (LD$_{50}$)

Swiss Nos (Nossan, Correzzana, Milano) mice, weighing 18 to 20 g each, on an empty stomach for 18 hours with water "ad libitum" and kept in cages with grid floor, were used. The animals, divided into groups of 10 animals each, (5M+5F) were treated intraperitoneally (10 ml/kg) with the compounds under examination dissolved in water or suspended in 0.5% carboxymethylcellulose. The animals were kept in the cages and the mortality occurred within the following 6 hours was noted down. At the expiring of the 6 hours the animals were allowed to eat up to the end of the experimentation which lasted 14 days. During this period all the toxic symptoms and the mortality occuring were noted.

The animals which died during the test period and those which were sacrificed at the end of the same, underwent autopsy for a macroscopic examination of their main organs. The experimental data were statistically compared with the $X^2$ method and LD$_{50}$ was extrapolated by the 'probit' method.

The data resulting from the tests carried out on some significant compounds of the class (I), evaluated in comparison to the well known antihistaminic compound Terfenadine, are given in the following Table.

TABLE

| Compound | Mortality induced by hystamine ED$_{50}$ p.o. μg/kg | Mortality induced by 48/80 ED$_{50}$ i.p. μg/kg | Increase of sleeping time induced by pentobarbital 25 mg/kg increase % | Acute toxicity LD$_{50}$ i.p. mg/kg |
|---|---|---|---|---|
| Example 1 | 30 | 500 | 10 | >100 |
| Example 2 | 25 | 300 | 7 | >100 |
| Example 9 | 3 | 500 | 43 | >100 |
| Terfenadine | 436 | 1090 | 44 | 620 |

For therapeutic administration, the compounds according to the present invention are used in the form of pharmaceutical preparations which contain said compounds in admixture with pharmaceutically acceptable carriers such as an organic or inorganic solid or liquid excipient suitable for oral or parenteral administration. The compounds of the invention may be contained in these pharmaceutical preparations in the form of free base or in the form of their non-toxic acid addition salts. The inorganic acids which may be employed to prepare these acid addition salts may be, e.g., hydrochloric or sulphuric acid. The organic acids which may be employed are, e.g., maleic, fumaric and succinic acid.

The pharmaceutical preparations may be in solid form as capsules, tablets, dragees or in liquid form such as solutions, suspensions or emulsions. If desired, there may be included in the above preparations auxiliary substances such as stabilizing agents and other commonly used additives, or there may be contained other therapeutically active agents suitable to be administered together with the compounds of the invention. The dosage of the compounds will vary from the administration route and will also depend upon the age and condition of the patient.

The following Examples have the purpose of illustrating the invention without limiting it.

EXAMPLE 1

3-(2-Ethoxyethyl)-2-(3-dimethylaminopropyl)-3H-imidazo [4,5-b] pyridine

A mixture formed by 8.4 g 2,3-diaminopyridine and by 14.2 g 4-dimethylaminobutyric acid hydrochloride in 60 g polyphosphoric acid, is heated at 160° C. for 2 hours. Then it is cooled to 80° C., diluted with water and cooled to room temperature. The reaction mixture is adjusted to pH 10 by adding NaOH, it is extracted with chloroform and the organic phase is evaporated to dryness to obtain 4.4 g of a waxy product consisting of 2-(3-dimethylaminopropyl)-3H-imidazo [4,5-b] pyridine.

| Elementary analysis for $C_{11}H_{16}N_4$ | | | |
|---|---|---|---|
| | C | H | N |
| calculated % | 64.68 | 7.89 | 27.43 |
| found % | 64.51 | 7.87 | 27.31 |

To a solution formed by 2.9 g 2-(3-dimethylaminopropyl)-3H-imidazo [4,5-b] pyridine in 10 ml N,N-dimethylformamide, 0.85 g 60% sodium hydride are added in portions and then, dropwise, a solution formed by 2 g 2-ethoxyethyl chloride in 3 ml N,N-dimethylformamide. The reaction mixture is then heated at 100° C. for 2 hours, cooled to room temperature and diluted with a small amount of water. Extraction is made several times with diethyl ether, ethereal extracts are collected together, evaporated to dryness and the obtained residue is purified by chromatography on silicagel column (CHCl$_3$—CH$_3$OH 9:1). The fractions which contain the product are evaporated to dryness and from the obtained residue, dissolved in ethyl alcohol and treated with hydrocloric acid, 2.5 g 3-(2-ethoxyethyl)-2-(3-dimethylaminopropyl)-3H-imidazo [4,5-b] pyridine dihydrochloride melting at 165°-167° C. crystallize.

EXAMPLE 2

3-(2-Ethoxyethyl)-2-(2-dimethylaminoethyl)-3H-imidazo [4,5-b] pyridine

A mixture formed by 3.9 g 2,3-diaminopyridine and 6.1 g 3-dimethylaminopropionic acid hydrochloride in 40 g polyphosphoric acid, is heated at 160° C. for 5 hours. Reaction mixture is cooled to room temperature, dissolved in water, then made alkaline adjusting the pH to 10 with NaOH and extracted several times with chloroform. Organic extracts are collected together, evaporated to dryness and the residue, crystallized from acetonitrile, gives 1.4 g 2-(2-dimethylaminoethyl)-3H-imidazo [4,5-b] pyridine melting at 109°-112° C. Operation is further processed as described in Example 1 using 2-(2-dimethylaminoethyl)-3H-imidazo [4,5-b] pyridine and 2-ethoxyethyl chloride and after purification by chromatography on silicagel column (CHCl$_3$—CH$_3$OH 9:1), 3-(2-ethoxyethyl)-2-(2-dimethylaminoethyl)-3H-imidazo [4,5-b] pyridine is obtained as an oil with a yield of 17%.

| Elementary analysis for C$_{14}$H$_{22}$N$_4$O | | | |
|---|---|---|---|
| | C | H | N |
| calculated % | 64.9 | 8.45 | 21.35 |
| found % | 64.32 | 8.37 | 21.32 |

EXAMPLE 3

3-(2-Ethoxyethyl)-2-(3-diethylaminopropyl)-3H-imidazo [4,5-b] pyridine difumarate Operation is carried out similarly to what previously described in Example 2 using 4-diethylaminobutyric acid hydrochloride to obtain, at first, 2-(3-diethylaminopropyl)-3H-imidazo [4,5-b] pyridine melting at 56°–58° C. (yield 77%) and, then 3-(2-ethoxyethyl)-2-(3-diethylaminopropyl)-3H-imidazo [4,5-b] pyridine difumarate melting at 120°–121° C. (acetone). Yield 24%.

EXAMPLE 4

3-(2-Ethoxyethyl)-2-dimethylaminomethyl-3H-imidazo [4,5-b] pyridine

Operation is carried out similarly to what described in Example 2 using dimethylaminoacetic acid hydrochloride to obtain at first, 2-dimethylaminomethyl-3H-imidazo [4,5-b] pyridine melting at 123°–125° C. and, then 3-(2-ethoxyethyl)-2-dimethylaminomethyl-3H-imidazo [4,5-b] pyridine as an oil, after purification by chromatography on silicagel column (CHCl$_3$—CH$_3$OH 9:1). Yield 25%.

| Elementary analysis for C$_{13}$H$_{20}$N$_4$O | | | |
|---|---|---|---|
| | C | H | N |
| calculated % | 62.88 | 8.12 | 22.56 |
| found % | 62.91 | 7.98 | 22.47 |

EXAMPLE 5

3-(2-Ethoxyethyl)-2-(4-dimethylaminobutyl)-3H-imidazo [4,5-b] pyridine

Operation is carried out similarly to what described in Example 2 using 5-dimethylaminopentanoic acid hydrochloride to obtain, at first, 2-(4-dimethylaminobutyl)-3H-imidazo [4,5-b] pyridine as a waxy solid. Yield 45%.

| Elementary analysis for C$_{12}$H$_{18}$N$_4$ | | | |
|---|---|---|---|
| | C | H | N |
| calculated % | 66.02 | 8.31 | 25.66 |
| found % | 65.84 | 8.38 | 25.81 | and, then 3-(2-ethoxyethyl)-2-(4-dimethylaminobutyl)-3H-imidazo [4,5-b] pyridine, as an oil, after purification by chromatography on silicagel column (CHCl$_3$—CH$_3$OH 9:1). Yield 22%.

| Elementary analysis for C$_{16}$H$_{26}$N$_4$O | | | |
|---|---|---|---|
| | C | H | N |
| calculated % | 66.18 | 9.02 | 19.29 |
| found % | 66.33 | 9.18 | 19.02 |

EXAMPLE 6

3-(2-Ethoxyethyl)-2-(5-dimethylaminopentyl)-3H-imidazo [4,5-b] pyridine

Operation is carried out similarly to what described in Example 2 using 6-dimethylaminohexanoic acid hydrochloride to obtain, at first, 2-(5-dimethylaminopentyl)-3H-imidazo [4,5-b] pyridine as a waxy solid. Yield 65%.

| Elementary analysis for C$_{13}$H$_{20}$N$_4$ | | | |
|---|---|---|---|
| | C | H | N |
| calculated % | 67.21 | 8.68 | 24.11 |
| found % | 67.20 | 8.71 | 24.00 | and, then 3-(2-ethoxyethyl)-2-(5-dimethylaminopentyl)-3H-imidazo [4,5-b] pyridine as an oil, after purification by chromatography on silicagel column (CHCl$_3$—CH$_3$OH 9:1). Yield 15%.

| Elementary analysis for C$_{17}$H$_{28}$N$_4$O. | | | |
|---|---|---|---|
| | C | H | N |
| calculated % | 67.07 | 9.27 | 18.40 |
| found % | 66.74 | 9.35 | 18.39 |

EXAMPLE 7

3-(2-Ethoxyethyl)-2-[3-(pyrrolidin-1-yl)propyl]-3H-imidazo [4,5-b] pyridine difumarate Operation is carried out similarly to what previously described in Example 2 using 4-(pyrrolidin-1-yl) butyric acid hydrochloride to obtain, first, 2-[3-(pyrrolidin-1-yl)propyl]-3H-imidazo [4,5-b] pyridine as an oil after purification by chromatography on silicagel column (CHCl$_3$—CH$_3$OH 95:5). Yield 72%.

| Elementary analysis for C$_{13}$H$_{18}$N$_4$ | | | |
|---|---|---|---|
| | C | H | N |
| calculated % | 67.80 | 7.88 | 24.33 |
| found % | 68.12 | 7.92 | 24.20 | and then 3-(2-ethoxyethyl)-2-[3-(pyrrolidin-1-yl)propyl]-3H-imidazo [4,5-b] pyridine difumarate melting at 150°–152° C. Yield 19%.

EXAMPLE 8

3-(2-Ethoxyethyl)-2-[(pyrrolidin-1-yl)methyl]-3H-imidazo [4,5-b] pyridine

Operation is carried out similarly to what previously described in Example 2 using pyrrolidin-1-ylacetic acid hydrochloride to obtain, first 2-[(pyrrolidin-1-yl)methyl]-3H-imidazo [4,5-b] pyridine melting at 134°–136° C. (acetonitrile), with a yield of 33%, and then, 3-(2-ethoxyethyl)-2-[(pyrrolidin-1-yl)methyl]-3H-imidazo [4,5-b] pyridine as an oil after purification by chromatography on silicagel column (CHCl$_3$—CH$_3$OH 9:1). Yield 21%.

| Elementary analysis for C$_{15}$H$_{22}$N$_4$O. | | | |
|---|---|---|---|
| | C | H | N |
| calculated % | 65.67 | 8.08 | 20.42 |
| found % | 65.60 | 7.92 | 20.44 |

EXAMPLE 9

3-(2-Ethoxyethyl)-2-[3-(morpholin-4-yl)propyl]-3H-imidazo [4,5-b] pyridine difumarate.

Operation is carried out similarly to what described in Example 2 using 4-(morpholin-4-yl) butyric acid hydrochloride to obtain, at first 2-[3-(morpholin-4-yl)propyl]-3H-imidazo [4,5-b] pyridine melting at 101°-103° C. (diethyl ether), yield 42%, and then, 3-(2-ethoxyethyl)-2-[3-(morpholin-4-yl)propyl]-3H-imidazo [4,5-b] pyridine difumarate melting at 171°-173° C. (acetone). Yield 15%.

EXAMPLE 10

3-(2-Ethoxyethyl)-2-(3-diallylaminopropyl)-3H-imidazo [4,5-b] pyridine

Operation is carried out similarly to what previously described in Example 2 using 4-diallylaminobutyric acid hydrochloride to obtain, first, 2-(3-diallylaminopropyl)-3H-imidazo [4,5-b] pyridine and, then, 3-(2-ethoxyethyl)-2-(3-diallylaminopropyl)-3H-imidazo [4,5-b] pyridine as an oil.

| Elementary analysis for C$_{19}$H$_{28}$N$_4$. | | | |
|---|---|---|---|
| | C | H | N |
| calculated % | 69.48 | 8.59 | 17.06 |
| found % | 69.32 | 8.70 | 16.91 |

EXAMPLE 11

3-(2-Ethoxyethyl)-2-[3-(piperidin-1-yl)propyl]-3H-imidazo [4,5-b] pyridine difumarate Operation is carried out similarly to which described in Example 2 using 4-(piperidin-1-yl) butyric acid hydrochloride to obtain, at first, 2-[3-(piperidin-1-yl)propyl]-3H-imidazo [4,5-b] pyridine as an oil, after purification by chromatography on silicagel column (CHCl$_3$—CH$_3$OH-cyclohexane-NH$_4$OH 68:15:15:0.2). Yield 35%.

| Elementary analysis for C$_{14}$H$_{20}$N$_4$. | | | |
|---|---|---|---|
| | C | H | N |
| calculated % | 68.82 | 8.25 | 22.93 |
| found % | 68.81 | 8.33 | 23.02 | and then, 3-(2-ethoxyethyl)-2-[3-(piperidin-1-yl)propyl]-3H-imidazo [4,5-b] pyridine difumarate melting at 148°-150° C. (acetone). Yield 24%.

What is claimed is:

1. A 2-substituted 3-(2-ethoxyethyl)imidazo [4,5-b] pyridine compound of the formula

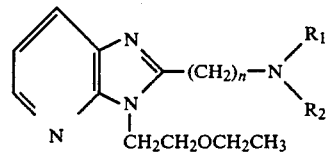

wherein n is an integer of from 1 to 5 inclusive, and R$_1$ and R$_2$ each represents a saturated or unsaturated alkyl radical containing from 1 to 4 carbon atoms or they may form, together with the adjacent nitrogen atom, a heterocyclic ring selected from the group consisting of pyrrolidine, morpholine and piperidine, wherein said heterocyclic ring may be substituted by a C$_1$-C$_3$ alkyl group, or a non-toxic pharmaceutically acceptable acid addition salt thereof.

2. A 2-substituted 3-(2-ethoxyethyl)imidazo [4,5-b] pyridine compound according to claim 1, wherein —N(R$_1$)R$_2$ represents a morpholine ring.

3. A 2-substituted 3-(2-ethoxyethyl)imidazo [4,5-b] pyridine compound according to claim 1 wherein R$_1$ and R$_2$ each represent a methyl radical.

4. 3-(2-Ethoxyethyl)-2-(3-dimethylaminopropyl)-3H-imidazo [4,5-b] pyridine or a non-toxic pharmaceutically acceptable acid addition salt thereof.

5. 3-(2-Ethoxyethyl)-2-(2-dimethylaminoethyl)-3H-imidazo [4,5-b] pyridine or a non-toxic pharmaceutically acceptable acid addition salt thereof.

6. 3-(2-Ethoxyethyl)-2-[3-(morpholin-4-yl)propyl]-3H-imidazo [4,5-b] pyridine or a non-toxic pharmaceutically acceptable acid addition salt thereof.

7. A pharmaceutical composition comprising an antihistaminic effect amount of one or more compounds according to any of claims 1 to 6 in admixture with suitable pharmaceutically acceptable diluents.

* * * * *